United States Patent [19]

Chang et al.

[11] Patent Number: 5,288,927
[45] Date of Patent: Feb. 22, 1994

[54] PARA-SELECTIVE BUTYLATION OF PHENOL OVER FAIRLY LARGE-PORE ZEOLITES

[75] Inventors: Clarence D. Chang, Princeton, N.J.; Stuart D. Hellring, Yardley, Pa.

[73] Assignee: Mobil Oil Corp., Fairfax, Va.

[21] Appl. No.: 11,574

[22] Filed: Feb. 1, 1993

[51] Int. Cl.$^5$ .................. C07C 37/14; C07C 37/16
[52] U.S. Cl. .................. 568/789; 568/784; 568/785; 568/786
[58] Field of Search ............ 568/789, 790, 794, 795, 568/786, 785

[56] References Cited

U.S. PATENT DOCUMENTS

| | | | |
|---|---|---|---|
| 4,283,573 | 8/1981 | Young | 568/794 |
| 4,391,998 | 7/1983 | Wu | 568/781 |
| 4,405,818 | 9/1983 | Stead et al. | 568/781 |
| 4,954,663 | 9/1990 | Marler et al. | 568/791 |
| 5,072,054 | 12/1991 | Marler et al. | 568/794 |
| 5,175,375 | 12/1992 | Chang et al. | 568/781 |

OTHER PUBLICATIONS

Corma, A. et al., "Influence of the Acid-strength Distribution of the Zeolite Catalyst on the t-Butylation of Phenol," J. Chem. Research(s), 40-41 (1988).
Chemical Abstracts 107:58245c, vol. 107, 666 (1987).
Chemical Abstracts 109:170020t, vol. 109, 679 (1988).
Chemical Abstracts 112:157859r, vol. 112, 681 (1990).

Primary Examiner—Werren B. Lone
Attorney, Agent, or Firm—Alexander J. McKillop; Dennis P. Santini; Edward F. Kenehan, Jr.

[57] ABSTRACT

There is provided a process for reacting phenol with butene or butanol over fairly large-pore zeolites to give butylphenol with high para-selectivity. Particular zeolites for use in this reaction include ZSM-12 and zeolite beta. A particular butene or butanol reactant is isobutanol. The product of this reaction may have a high content of the mono-alkylated, tert-butyl product.

8 Claims, No Drawings

PARA-SELECTIVE BUTYLATION OF PHENOL OVER FAIRLY LARGE-PORE ZEOLITES

BACKGROUND

There is provided a process for reacting phenol with butene or butanol over fairly large-pore zeolites to give butylphenol with high para-selectivity.

Butylphenols are commodity chemicals in wide use as antioxidants in fuels, lubes, polymers and food. sec-Butylphenol can be oxidized to give dihydroxybenzenes and methylethylketone.

U.S. Pat. No. 4,391,998 describes the alkylation of phenol with isopropanol over certain medium-pore zeolites, such as ZSM-5. The isopropylphenol product of this ZSM-5 catalyzed reaction is primarily the para-isomer.

U.S. Pat. No. 5,175,375 describes the alkylation of phenol with isopropanol over ZSM-12 or zeolite beta. The isopropylphenol product of this ZSM-12 or zeolite beta catalyzed reaction is primarily the ortho-isomer.

SUMMARY

There is provided a process for preparing butylphenol, said process comprising reacting phenol with butene or butanol over a catalyst under conditions sufficient to produce said butylphenol, said catalyst comprising a zeolite having a Constraint Index of from 1 to 3.

There is also provided a process for preparing butylphenol, said process comprising reacting phenol with butene or butanol over a catalyst under conditions sufficient to produce said butylphenol, said catalyst comprising a zeolite selected from the group consisting of ZSM-12, zeolite beta and MCM-22.

DESCRIPTION

It has been discovered that phenol reacts with butene or butanol over acidic, fairly large-pore zeolites, such as zeolite beta, ZSM-12 and MCM-22, inter alia, to give butylphenol with high para-selectivity.

Based on studies conducted in the gas phase, it was discovered that para-butylphenol is the kinetically preferred product of the reaction of phenol with butene or butanol. In accordance with inventive subject matter described herein, it was further discovered that this kinetic product was produced in high selectivity when fairly large-pore zeolites, such as zeolite beta and ZSM-12, were used to catalyze this reaction. Without wishing to be bound by any particular theory or mode of operation, it is theorized that, when a fairly large-pore zeolite is used as a catalyst in this reaction, the diffusion of the bulky product from the surface of the catalyst is not restricted.

Another concern in aromatic alkylation involves the selectivity to mono-substituted products versus di- and other multi-substituted products. In the present reaction, it has been discovered that the zeolite catalyst restricts the formation of bulky multi-substituted products without interfering with the formation of mono-substituted products.

A convenient measure of the extent to which a zeolite provides control of access to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g., less than 5 Angstroms. On the other hand, zeolites which provide relatively free access to the internal zeolite structure have a low value for the Constraint Index, and usually pores of large size, e.g., greater than 8 Angstroms. The method by which Constraint Index is determined is described fully in U.S. Pat. No. 4,016,218, incorporated herein by reference for details of the method.

A zeolite which may be used in the present reaction may be a fairly large-pore zeolite. This zeolite may have a Constraint Index of 1 to 3. Zeolites having a Constraint Index of 3–12 are generally regarded to be medium-pore size zeolites. Zeolites having a Constraint Index of less than 1 are generally regarded to be large-pore size zeolites. Zeolites having a Constraint Index of 1–3 are defined herein as fairly large-pore size zeolites. These fairly large-pore size zeolites may be regarded as being in the large end of the scale of zeolites which are generally regarded to be medium-pore size zeolites.

The members of the class of medium-pore size zeolites may have an effective pore size of generally from about 5 to about 8 Angstroms, such as to freely sorb normal hexane. In addition, the structures provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the medium-pore size type. Windows of 10-membered rings are preferred, although, in some instances, excessive puckering of the rings or pore blockage may render these zeolites ineffective.

Although 12-membered rings in theory would not offer sufficient constraint to constitute a medium-size pore, it is noted that the puckered 12-ring structure of TMA offretite does show some constrained access. Other 12-ring structures may exist which may be regarded to be medium-pore sized, and therefore, it is not the present intention to classify a particular zeolite solely from theoretical structural considerations.

Constraint Index (CI) values for some typical materials are:

| | CI (at test temperature) | |
|---|---|---|
| ZSM-4 | 0.5 | (316° C.) |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |
| ZSM-34 | 50 | (371° C.) |
| ZSM-35 | 4.5 | (454° C.) |
| ZSM-38 | 2 | (510° C.) |
| ZSM-48 | 3.5 | (538° C.) |
| ZSM-50 | 2.1 | (427° C.) |
| MCM-22 | 1.5 | (454° C.) |
| TMA Offretite | 3.7 | (316° C.) |
| TEA Mordenite | 0.4 | (316° C.) |
| Mordenite | 0.5 | (316° C.) |
| Clinoptilolite | 3.4 | (510° C.) |
| REY | 0.4 | (316° C.) |
| Amorphous Silica-alumina | 0.6 | (538° C.) |
| Dealuminized Y (Deal Y) | 0.5 | (510° C.) |
| Erionite | 38 | (316° C.) |
| Zeolite Beta | 0.6–2.0 | (316° C.–399° C.) |

The above-described Constraint Index provides a definition of those zeolites which are particularly useful in the present process. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g., temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of particular interest herein of 1 to 3.

Examples of zeolites having a Constraint Index of from 1 to 3 include ZSM-12, zeolite beta and MCM-22.

ZSM-12 is described in U.S. Pat. No. 3,832,449. That description, and in particular the X-ray diffraction pattern disclosed therein, is incorporated herein by reference.

Zeolite beta is described in U.S. Pat. Nos. 3,308,069, and Re. No. 28,341, to which reference is made for details of this catalyst.

MCM-22 is described in U.S. Pat. No. 4,954,325, as well as in U.S. Pat. No. 5,072,054, the entire disclosures of which are expressly incorporated herein by reference.

The zeolite crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the zeolite with another material which is resistant to the temperatures and other conditions employed in the present process. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with zeolite crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

In addition to the foregoing materials, the crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In the reaction zone, the reaction temperature may be at least 25° C., e.g., from 25° C. to 450° C., e.g., from 200° C. to 300° C. Pressures range from 0 up to 5000 psig. The preferred range is from 0 to 400 psig. Liquid hourly space velocity may be from 0.1 to 5 $hr^{-1}$, more usually 0.5 to 2.

The amounts of reactants in the reaction zone may be sufficient amounts, e.g., amounts which are sufficient to produce the desired amount of product. Particular butanol reactants include isobutanol and t-butanol.

Phenol butylations were conducted using a feed solution of 56 wt. % phenol in isobutanol for a phenol-/isobutanol=1 (molar). Isobutanol was chosen as a isobutylene precursor since its use avoided the experimental difficulties of feeding pure phenol in a preheated pump on a laboratory scale. A stainless steel fixed-bed reactor (0.25 in. O.D. ×0.35 in. wall) was used with 3 ml zeolite zones by vycor. Hydrocarbons were analyzed by gc using a DB-1 capillary column. Regioisomers were separated using a 80/120 carbopak B/3% SP-1500 stainless steel packed column. FID response factors were determined using appropriate standards.

ZSM-12 was used as an alumina extrudate (65% zeolite, $SiO_2/Al_2O_3=250$). Zeolite beta was also used as an alumina extrudate (50% zeolite).

Data showing product distributions for ZSM-12 and zeolite beta under various operating conditions is shown in Table 1.

TABLE 1

| | Selective Phenol Butylation over Zeolites | | | | | | |
|---|---|---|---|---|---|---|---|
| | Zeolite | | | | | | |
| | ZSM-12 | ZSM-12 | Zeolite Beta | Zeolite Beta | Zeolite Beta | Zeolite Beta | Zeolite Beta |
| Temperature | 250 | 250 | 250 | 300 | 250 | 250 | 350 |
| Pressure | 300 | 300 | 0 | 0 | 300 | 0 | 300 |
| LHSV | 1 | 2 | 2 | 2 | 1 | 1 | 1 |
| Product Distribution (wt. %) | | | | | | | |
| Isobutanol | 0.37 | 0.07 | 1.20 | 0.02 | 0.19 | 0.27 | 0.80 |
| Phenol | 26.65 | 26.81 | 50.42 | 47.06 | 25.20 | 45.79 | 42.42 |
| Butenes | 2.51 | 3.01 | 18.68 | 22.96 | 1.97 | 18.79 | 7.58 |
| tert-Butylphenols | | | | | | | |
| ortho | 0.90 | 1.99 | 0.90 | 0.50 | 1.82 | 1.35 | 1.38 |
| meta | 11.83 | 6.67 | 2.69 | 1.23 | 7.14 | 3.26 | 0.37 |
| para | 10.11 | 22.59 | 6.24 | 2.81 | 24.87 | 9.12 | 2.90 |
| Other Butylphenols | 18.45 | 15.07 | 3.67 | 5.79 | 10.37 | 4.32 | 13.17 |
| Di(tert-Butyl)phenols | 5.54 | 4.36 | 0.80 | 0.41 | 9.18 | 1.52 | 2.23 |
| Other Products | 12.95 | 8.72 | 4.71 | 8.52 | 8.55 | 4.87 | 18.46 |
| Water | 10.70 | 10.71 | 10.69 | 10.71 | 10.71 | 10.71 | 10.70 |
| Total | 100.00 | 100.00 | 100.00 | 100.00 | 100.00 | 100.00 | 100.00 |
| Normalized tert-Butylphenols (%) | | | | | | | |
| ortho | 3.93 | 6.36 | 9.17 | 10.98 | 5.39 | 9.84 | 29.60 |
| meta | 51.80 | 21.34 | 27.34 | 27.05 | 21.10 | 23.73 | 7.90 |
| para | 44.26 | 72.30 | 63.49 | 61.97 | 73.51 | 66.43 | 62.50 |
| Mono/Di tert-Butylphenols | 4.12 | 7.16 | 12.33 | 11.10 | 3.68 | 9.03 | 2.08 |
| Isobutanol Conversion (%) | 99.15 | 99.84 | 97.28 | 99.96 | 99.58 | 99.40 | 98.19 |
| Phenol Conversion (%) | 52.42 | 52.13 | 9.97 | 15.96 | 54.99 | 18.23 | 24.25 |

ZSM-12 gave 72% para-tert-butylphenol in the tert-butylphenols at 52% phenol conversion. Zeolite beta similarly gave 73% para-tert-butylphenol in the tert-butylphenols at 55%.

The ratio of mono- to di-substituted tert-butylphenols was about 4 for both ZSM-12 and zeolite beta at 52-55% conversion. This ratio could be increased to as high as 12 by lowering conversion to about 10%. Further improvements could result from increasing the phenol/$C_4$ feed ratio.

What is claimed is:

1. A process for preparing para-tert-butylphenol, said process comprising reacting phenol with butene or butanol over a catalyst under conditions sufficient to produce said para-tert-butylphenol, said catalyst comprising a zeolite having a Constraint Index of from 1 to 3, wherein said conditions include a temperature of at least 25° C., a pressure of from 0 up to 5000 psig, and a liquid hourly space velocity of from 0.1 to 5 hr$^{-1}$.

2. A process according to claim 1, wherein isobutanol is selected as the butene or butanol reactant.

3. A process for preparing para-tert-butylphenol, said process comprising reacting phenol with butene or butanol over a catalyst under conditions sufficient to produce said para-tert-butylphenol, said catalyst comprising a zeolite selected from the group consisting of ZSM-12, zeolite beta and MCM-22, wherein said conditions include a temperature of at least 25° C., a pressure of from 0 up to 5000 psig, and a liquid hourly space velocity of from 0.1 to 5 hr$^{-1}$.

4. A process according to claim 3, wherein said zeolite is ZSM-12.

5. A process according to claim 3, wherein said zeolite is zeolite beta.

6. A process according to claim 3, wherein isobutanol is selected as the butene or butanol reactant.

7. A process according to claim 3, wherein said conditions include a temperature of from 25° C. to 450° C., a pressure of from 0 to 400 psig, and a liquid hourly space velocity of from 0.5 to 2 hr$^{-1}$.

8. A process according to claim 7, wherein said conditions include a temperature of from 200° C. to 300° C.

* * * * *